United States Patent
Cao et al.

(10) Patent No.: US 12,247,235 B2
(45) Date of Patent: *Mar. 11, 2025

(54) LIQUID FORMATION COMPRISING GH10 XYLANASE AND GH62 ARABINOFURANOSIDASE

(71) Applicant: NOVOZYMES A/S, Bagsvaerd (DK)

(72) Inventors: Yi Cao, Beijing (CN); Yu Zhang, Beijing (CN); Bernardo Vidal, Jr., Wake Forest, NC (US); Randall Scott Deinhammer, Wake Forest, NC (US); Mary Ann Stringer, Soborg (DK); Ye Liu, Beijing (CN); Purna Venkatesh, Bangalore (DK); Cui Liu, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 486 days.

This patent is subject to a terminal disclaimer.

(21) Appl. No.: 17/316,811

(22) Filed: May 11, 2021

(65) Prior Publication Data

US 2021/0261996 A1   Aug. 26, 2021

Related U.S. Application Data

(63) Continuation of application No. 16/341,214, filed as application No. PCT/CN2017/112865 on Nov. 24, 2017, now Pat. No. 11,180,786.

(30) Foreign Application Priority Data

Nov. 25, 2016  (WO) ................ PCT/CN2016/107281

(51) Int. Cl.
| | |
|---|---|
| C12N 9/20 | (2006.01) |
| A01H 5/10 | (2018.01) |
| C08B 30/04 | (2006.01) |
| C11B 1/02 | (2006.01) |
| C11B 1/10 | (2006.01) |
| C12N 9/24 | (2006.01) |
| C12N 9/42 | (2006.01) |
| C12P 19/02 | (2006.01) |
| C12P 19/04 | (2006.01) |
| C12P 19/14 | (2006.01) |
| C13K 1/06 | (2006.01) |

(52) U.S. Cl.
CPC ............... *C12P 19/04* (2013.01); *A01H 5/10* (2013.01); *C08B 30/04* (2013.01); *C11B 1/025* (2013.01); *C11B 1/10* (2013.01); *C12N 9/2402* (2013.01); *C12N 9/2434* (2013.01); *C12N 9/248* (2013.01); *C12N 9/2482* (2013.01); *C12P 19/02* (2013.01); *C12P 19/14* (2013.01); *C12Y 302/01008* (2013.01); *C12Y 302/01055* (2013.01); *C13K 1/06* (2013.01)

(58) Field of Classification Search
CPC .......... C12N 9/248; C12N 9/2437; C12Y 302/01055; C12Y 302/01; C12Y 301/01072; Y02E 50/10; C12P 19/14

USPC .................................................. 435/200, 161
See application file for complete search history.

(56) References Cited

U.S. PATENT DOCUMENTS

| | | |
|---|---|---|
| 5,066,218 A | 11/1991 | Silver |
| 5,693,518 A | 12/1997 | Kofod |
| 6,562,340 B1 | 5/2003 | Bedford |
| 6,566,125 B2 | 5/2003 | Johnson |
| 7,666,648 B2 | 2/2010 | Foreman et al. |
| 10,711,259 B2 | 7/2020 | Peng |
| 11,180,786 B2 | 11/2021 | Cao et al. |
| 2008/0171360 A1 | 7/2008 | Lange |
| 2008/0274527 A1* | 11/2008 | Soerensen et al. |
| 2009/0117630 A1 | 5/2009 | Olsen |
| 2009/0136476 A1 | 5/2009 | Soerensen et al. |
| 2009/0148901 A1 | 6/2009 | Lopez de Leon et al. |
| 2009/0220480 A1 | 9/2009 | Gray |
| 2010/0189706 A1 | 7/2010 | Chang et al. |
| 2011/0078830 A1 | 3/2011 | Tang et al. |
| 2011/0086408 A1 | 4/2011 | Power |
| 2011/0131687 A1 | 6/2011 | Maranta et al. |
| 2012/0040410 A1 | 2/2012 | Prade et al. |
| 2014/0273119 A1 | 9/2014 | Liu et al. |
| 2014/0287465 A1 | 9/2014 | Spodsberg et al. |
| 2015/0315297 A1 | 11/2015 | Han |
| 2017/0335302 A1 | 11/2017 | Peng |
| 2019/0002592 A1 | 1/2019 | Cao |
| 2020/0291372 A1 | 9/2020 | Peng et al. |

(Continued)

FOREIGN PATENT DOCUMENTS

| | | |
|---|---|---|
| AU | 2011239240 | 10/2011 |
| AU | 2011239240 A1 | 11/2011 |
| WO | 94/21785 A1 | 9/1994 |

(Continued)

OTHER PUBLICATIONS

Laothanachareon et al Bioresource Technol 2015, 198, pp. 682-690.*
Yang et al, 2015, Appl Biochem Biotechnol 175, 1960-1970.
Agger et al., J. Agric. Food Chem., vol. 58, pp. 6141-6148 (2010).
Chica et al., Current Opinion in Biotechnology, vol. 16, pp. 378-384 (2005).
Hashimoto et al., Journal of Bioscience and Bioengineering, vol. 95, No. 2, pp. 164-169 (2003).
Huismann et al., Carbohydrate Polymers, vol. 43, pp. 269-279 (2000).

(Continued)

*Primary Examiner* — Robert B Mondesi
*Assistant Examiner* — Mohammad Y Meah

(57) ABSTRACT

The present invention relates to an improved process of treating crop kernels to provide a starch product of high quality suitable for conversion of starch into mono- and oligosaccharides, ethanol, sweeteners, etc. The present invention also relates to polypeptides having GH10 xylanase activity and polypeptides having GH62 arabinofuranosidase activity. Further, the present invention also relates to a process for extraction or separation of crude palm oil.

6 Claims, No Drawings

Specification includes a Sequence Listing.

(56) References Cited

U.S. PATENT DOCUMENTS

2021/0079368 A9  3/2021  Zhu et al.

FOREIGN PATENT DOCUMENTS

| | | | |
|---|---|---|---|
| WO | 96/23062 | A1 | 8/1996 |
| WO | 02/00731 | | 1/2002 |
| WO | 02/00910 | A2 | 1/2002 |
| WO | 02/00911 | | 1/2002 |
| WO | 02/02644 | | 1/2002 |
| WO | 2005/059084 | A1 | 6/2005 |
| WO | 2006125438 | A1 | 11/2006 |
| WO | 2009/018537 | | 2/2009 |
| WO | 2009073383 | A1 | 6/2009 |
| WO | 2009/108941 | | 9/2009 |
| WO | 2011/057140 | | 5/2011 |
| WO | 2011/153516 | | 12/2011 |
| WO | 2012/011130 | | 1/2012 |
| WO | 2012/103288 | | 8/2012 |
| WO | 2013/182669 | | 12/2013 |
| WO | 2014/082564 | A1 | 6/2014 |
| WO | 2014/202716 | | 12/2014 |
| WO | 2016/082771 | A1 | 6/2016 |
| WO | 2017088820 | A1 | 6/2017 |

OTHER PUBLICATIONS

Ichikawa et al., EBI Accession No. E4NJK0 (2011).
Jordan et al., Biochem. J., vol. 442, pp. 241-252 (2012).
Liu et al., UniProt Accession No. S7ZW00 (2014).
Nielsen et al., UniProt Accession No. A0A1V6NXM6 (2018).
Popper et al., Plant Physiology, vol. 153, pp. 373-383 (2010).
Rantanen et al., Carbohydrate Polymers, vol. 68, pp. 350-359 (2007).
Sakamoto et al., Appl. Microbiol. Biotechnol., vol. 90, pp. 137-146 (2011).
Sakamoto et al., UniProt Accession No. B5MGR2 (2014).
Singh et al., Current Protein and Peptide Science, vol. 18, pp. 1-11 (2017).
Soerensen et al., EBI Accession No. CS459135 (2007).
Wahl et al., Molecular hybridization of immobilized nucleic acids, vol. 152, pp. 399-407 (1987).
Gao et al., Grain Distribution Technology, vol. 6, pp. 36-42 (2012).
Kubicek et al., GenBank accession No. EHK20487 (2011).
Anonymous, NCBI Reference sequence XP_001389996.2 (2011).
Anonymous, NCBI Reference sequence WP_003231534.1 (2015).
Gielkens et al., GenBank Accession No. Z78010.1 (2006).
Johnston et al., Cereal Chemistry, vol. 81, No. 5, pp. 626-632 (2004).
Takahashi et al., Genbank Accession No. AB821370.1 (2013).
Futagami et al., EBI Accession No. G7Y053 (2016).
Pel et al., EBI Accession No. A2QFV9 (2010).
Anonymous, NCBI Reference sequence No. XP_001389998.1 (2011).
Futagami et al., GenBank Accession No. GAA92551.1 (2015).
He et al, 2015, Metallurgical industry press, 211.
Zhao, 2015, Food anti nutritional factor, China Agricultural University Press, 33-34.
Couturier et al., BMC Genomics, 2012, 1-14, 13(57).
Kaemper et al, 2014, Uniprot Access No. Q4P902.
Kamper et al, 2014, Uniprot Access No. Q4P6F4.
KAUR 2014 Microbiol Biotechnol 8(3) 419-433, 8(3).
OTTENHEIM_2016_EBI_Accession_No.__ A0AOS2CWJ5.
Fujii et al, 2022, Uniprot access No. A0A2H5BN17.
Moroz et al, 2018, Acta Cryst F74, 490-495.
Liao et al, 2013, GenBank No. AGW24288.1.
Berrin et al., Biotechnol Lett, 2008, 1139-1150, 30.
Fortune et al., BMC Biotechnol, 2019, 1-13, 19:22.
Kan et al. 2014, Modern Food Science and Technology 30, 42-46.
Berrin et al., Biotechnol Lett, 30, 1139-1150, 2008.
Fortune et al., BMC Biotechnol, 19: 22, 1-13, 2019.
Kan et al., Modern Food Science and Technology, 30(10), 42-46, 2014.
Kuo et al., 2015, Accession A0A0C3D2W4.

* cited by examiner

SEQUENCE LISTING

<160> NUMBER OF SEQ ID NOS: 6

<210> SEQ ID NO 1
<211> LENGTH: 332
<212> TYPE: PRT
<213> ORGANISM: Aspergillus Niger

<400> SEQUENCE: 1

```
Met Lys Phe Phe Asn Ala Lys Gly Ser Leu Leu Ser Ser Gly Ile Tyr
1               5                   10                  15

Leu Ile Ala Leu Thr Pro Phe Val Asn Ala Lys Cys Ser Leu Pro Ser
                20                  25                  30

Ser Tyr Ser Trp Ser Ser Thr Asp Ala Leu Ala Thr Pro Lys Ser Gly
            35                  40                  45

Trp Thr Ala Leu Lys Asp Phe Thr Asp Val Val Ser Asp Gly Lys His
        50                  55                  60

Ile Val Tyr Ala Ser Thr Thr Asp Glu Ala Gly Asn Tyr Gly Ser Met
65                  70                  75                  80

Thr Phe Gly Ala Phe Ser Glu Trp Ser Asn Met Ala Ser Ala Ser Gln
                85                  90                  95

Thr Ala Thr Pro Phe Asn Ala Val Ala Pro Thr Leu Phe Tyr Phe Lys
            100                 105                 110

Pro Lys Ser Ile Trp Val Leu Ala Tyr Gln Trp Gly Ser Ser Thr Phe
        115                 120                 125

Thr Tyr Arg Thr Ser Gln Asp Pro Thr Asn Val Asn Gly Trp Ser Ser
    130                 135                 140

Glu Gln Ala Leu Phe Thr Gly Lys Leu Ser Asp Ser Ser Thr Gly Ala
145                 150                 155                 160

Ile Asp Gln Thr Val Ile Gly Asp Asp Thr Asn Met Tyr Leu Phe Phe
                165                 170                 175

Ala Gly Asp Asn Gly Lys Ile Tyr Arg Ser Ser Met Ser Ile Asp Glu
            180                 185                 190

Phe Pro Gly Ser Phe Gly Ser Gln Tyr Glu Glu Ile Leu Ser Gly Ala
        195                 200                 205

Thr Asn Asp Leu Phe Glu Ala Val Gln Val Tyr Thr Val Asp Gly Gly
    210                 215                 220

Glu Gly Asn Ser Lys Tyr Leu Met Ile Val Glu Ala Ile Gly Ser Thr
225                 230                 235                 240

Gly His Arg Tyr Phe Arg Ser Phe Thr Ala Ser Ser Leu Gly Gly Glu
                245                 250                 255

Trp Thr Ala Gln Ala Ala Ser Glu Asp Lys Pro Phe Ala Gly Lys Ala
            260                 265                 270

Asn Ser Gly Ala Thr Trp Thr Glu Asp Ile Ser His Gly Asp Leu Val
```

Arg Asn Asn Pro Asp Gln Thr Met Thr Val Asp Pro Cys Asn Leu Gln
275                 280                 285
290                 295                 300

Leu Leu Tyr Gln Gly His Asp Pro Asn Ser Ser Gly Asp Tyr Asn Leu
305                 310                 315                 320

Leu Pro Trp Lys Pro Gly Val Leu Thr Leu Lys Gln
                325                 330

<210> SEQ ID NO 2
<211> LENGTH: 999
<212> TYPE: DNA
<213> ORGANISM: Aspergillus niger

<400> SEQUENCE: 2
atgaagttct tcaatgccaa aggcagcttg ctgtcatcag gaatttacct cattgcatta     60
accccctttg ttaacgccaa atgctctctt ccatcgtcct atagttggag ttcaaccgat    120
gctctcgcaa ctcctaagtc aggatggacc gcactgaagg actttactga tgttgtctcg    180
gacggcaaac atatcgtcta tgcgtccact actgatgaag cgggaaacta tggctcgatg    240
acctttggcg ccttctcaga gtggtcgaac atggcatctg ctagccagac agccaccccc    300
ttcaatgccg tggctcctac cctattctat ttcaagccga aaagcatctg ggttctggcc    360
taccaatggg gttccagtac attcacctac cgcacctccc aagatcccac caatgtcaat    420
ggctggtcgt cggagcaggc gcttttcacc ggaaaactca gcgactcaag caccggtgcc    480
attgaccaga cggtgattgg cgacgatacg aatatgtatc tcttctttgc cggcgacaac    540
ggcaagatct accgatccag catgtccatc gatgaatttc ccggaagctt cggcagccag    600
tacgaggaaa ttctgagtgg tgccaccaac gacctattcg aggcggtcca agtgtacacg    660
gttgacggcg gcgagggcaa cagcaagtac ctcatgatcg ttgaggcgat cgggtccact    720
ggacatcgtt atttccgctc cttcacggcc agcagtctcg gtggagagtg acagcccag    780
gcggcaagtg aggataaacc cttcgcaggc aaagccaaca gtggcgccac ctggaccgaa    840
gacattagcc atggtgactt ggttcgcaac aaccctgatc aaaccatgac tgtcgatcct    900
tgcaacctcc agttgctcta tcagggccat gaccccaaca gcagtggcga ctacaacctc    960
ttgccatgga agccgggcgt ccttaccttg aagcagtga                           999

<210> SEQ ID NO 3
<211> LENGTH: 332
<212> TYPE: PRT
<213> ORGANISM: Aspergillus Niger

<400> SEQUENCE: 3

Met Lys Phe Leu Lys Ala Lys Gly Ser Leu Leu Ser Ser Gly Ile Tyr
1               5                   10                  15

Leu Ile Ala Leu Ala Pro Phe Val Asn Ala Lys Cys Ala Leu Pro Ser
                20                  25                  30

Thr Tyr Ser Trp Thr Ser Thr Asp Ala Leu Ala Thr Pro Lys Ser Gly
            35                  40                  45

Trp Thr Ala Leu Lys Asp Phe Thr Asp Val Val Ser Asn Gly Lys His
        50                  55                  60

Ile Val Tyr Ala Ser Thr Thr Asp Thr Gln Gly Asn Tyr Gly Ser Met
65                  70                  75                  80

Gly Phe Gly Ala Phe Ser Asp Trp Ser Asp Met Ala Ser Ala Ser Gln
                85                  90                  95

```
Thr Ala Thr Ser Phe Ser Ala Val Ala Pro Thr Leu Phe Tyr Phe Gln
                100                 105                 110

Pro Lys Ser Ile Trp Val Leu Ala Tyr Gln Trp Gly Ser Ser Thr Phe
            115                 120                 125

Thr Tyr Arg Thr Ser Gln Asp Pro Thr Asn Val Asn Gly Trp Ser Ser
        130                 135                 140

Glu Gln Ala Leu Phe Thr Gly Lys Ile Ser Gly Ser Thr Gly Ala
145                 150                 155                 160

Ile Asp Gln Thr Val Ile Gly Asp Asp Thr Asn Met Tyr Leu Phe Phe
                165                 170                 175

Ala Gly Asp Asn Gly Lys Ile Tyr Arg Ser Ser Met Ser Ile Asn Asp
            180                 185                 190

Phe Pro Gly Ser Phe Gly Ser Gln Tyr Glu Glu Ile Leu Ser Gly Ala
        195                 200                 205

Thr Asn Asp Leu Phe Glu Ala Val Gln Val Tyr Thr Val Asp Gly Gly
    210                 215                 220

Glu Gly Asp Ser Lys Tyr Leu Met Ile Val Glu Ala Ile Gly Ser Thr
225                 230                 235                 240

Gly His Arg Tyr Phe Arg Ser Phe Thr Ala Ser Ser Leu Gly Gly Glu
                245                 250                 255

Trp Thr Ala Gln Ala Ala Ser Glu Asp Gln Pro Phe Ala Gly Lys Ala
            260                 265                 270

Asn Ser Gly Ala Thr Trp Thr Asp Asp Ile Ser His Gly Asp Leu Val
        275                 280                 285

Arg Asn Asn Pro Asp Gln Thr Met Thr Val Asp Pro Cys Asn Leu Gln
    290                 295                 300

Leu Leu Tyr Gln Gly His Asp Pro Asn Ser Asn Ser Asp Tyr Asn Leu
305                 310                 315                 320

Leu Pro Trp Lys Pro Gly Val Leu Thr Leu Lys Gln
                325                 330

<210> SEQ ID NO 4
<211> LENGTH: 319
<212> TYPE: PRT
<213> ORGANISM: Aspergillus Niger

<400> SEQUENCE: 4

Met Val Gln Ile Lys Val Ala Ala Leu Ala Met Leu Phe Ala Ser Gln
1               5                   10                  15

Val Leu Ser Glu Pro Ile Glu Pro Arg Gln Ala Ser Val Ser Ile Asp
            20                  25                  30

Thr Lys Phe Lys Ala His Gly Lys Lys Tyr Leu Gly Asn Ile Gly Asp
        35                  40                  45

Gln Tyr Thr Leu Thr Lys Asn Ser Lys Thr Pro Ala Ile Ile Lys Ala
    50                  55                  60

Asp Phe Gly Ala Leu Thr Pro Glu Asn Ser Met Lys Trp Asp Ala Thr
65                  70                  75                  80

Glu Pro Ser Arg Gly Gln Phe Ser Phe Ser Gly Ser Asp Tyr Leu Val
                85                  90                  95

Asn Phe Ala Gln Ser Asn Asn Lys Leu Ile Arg Gly His Thr Leu Val
            100                 105                 110

Trp His Ser Gln Leu Pro Ser Trp Val Gln Ser Ile Thr Asp Lys Asn
        115                 120                 125

Thr Leu Ile Glu Val Met Glu Asn His Ile Thr Thr Val Met Gln His
    130                 135                 140
```

Tyr Lys Gly Lys Ile Tyr Ala Trp Asp Val Val Asn Glu Ile Phe Asn
145                 150                 155                 160

Glu Asp Gly Ser Leu Arg Asp Ser Val Phe Tyr Lys Val Ile Gly Glu
            165                 170                 175

Asp Tyr Val Arg Ile Ala Phe Glu Thr Ala Arg Ala Ala Asp Pro Asn
        180                 185                 190

Ala Lys Leu Tyr Ile Asn Asp Tyr Asn Leu Asp Ser Ala Ser Tyr Pro
    195                 200                 205

Lys Leu Thr Gly Met Val Ser His Val Lys Lys Trp Ile Ala Ala Gly
210                 215                 220

Ile Pro Ile Asp Gly Ile Gly Ser Gln Thr His Leu Ser Ala Ala Leu
225                 230                 235                 240

Asn Ala Leu Ala Gly Ala Gly Thr Lys Glu Ile Ala Val Thr Glu Leu
                245                 250                 255

Asp Ile Ala Gly Ala Ser Ser Thr Asp Tyr Val Glu Val Val Glu Ala
            260                 265                 270

Cys Leu Asn Gln Pro Lys Cys Ile Gly Ile Thr Val Trp Gly Val Ala
        275                 280                 285

Asp Pro Asp Ser Trp Arg Ser Ser Ser Thr Pro Leu Leu Phe Asp Ser
    290                 295                 300

Asn Tyr Asn Pro Lys Pro Ala Tyr Thr Ala Ile Ala Asn Ala Leu
305                 310                 315

<210> SEQ ID NO 5
<211> LENGTH: 1495
<212> TYPE: DNA
<213> ORGANISM: Aspergillus niger

<400> SEQUENCE: 5

```
atggttcaga tcaaggtagc tgcactggcg atgcttttcg ctagccaggt actttctgag      60
cccattgaac cccgtcaggc ttcagtgagt attgatacca aattcaaggc tcacgggaag     120
aaatatcttg gaacattggt gatcagtac accttgacca agaactcgaa gactccggcc     180
attatcaagg ccgattttgg cgcgttgact ccagagaaca gcatgaagtg ggatgctact     240
gaacgtaagt acaatcccct catcattatc attgcgactc agactaaatc agaagtatag     300
ccagccgtgg acagttctct ttctcaggat cggactacct ggtacgtaca gcacttctca     360
acccttcact atagtcgtgc tcgaggctta cataacttag gtcaactttg cccagtctaa     420
caacaagctg atccgcggac atactctcgg tgagttttg acgtactagc gtgggaagca     480
taccaagaca gtgaagctaa actcaaccag tgtggcactc gcagctcccc tcctgggtcc     540
aatccatcac ggacaagaat acactgatcg aagtcatgga gaatcacatc accacagtga     600
tgcaacacta aagggcaag atttatgcct gggtaggctg tcacccatca acttctcaaa     660
agtgttatta ttaatcgtct taaggatgtt gtcaatgaaa tcttcaacga agacggctcc     720
ctacgcgaca gcgtcttta caaggtcatc ggcgaggact acgtgcggat cgccttcgag     780
actgctcggg ctgcagatcc caatgcaaag ctctacatca atgattacaa gtaagtcata     840
tttgcctctc tcctgttacc aattggatac taaatttgaa aagcctggat ccgcctcct     900
acctaaatt gaccggcatg ttagccatg tcaagaagtg gatcgcagct ggcatccta     960
tcgatggaat cggtaagccc cttgtgatca gatgttccg gctattattt ctcatctttc    1020
ttcaaaaggt tccaaacccc acttgagcgc tggtggaggt gctggaattt ctggataagt    1080
accccctccc ctttattctg gttgacgata gctgatagtc ccttacagct ctcaatgctc    1140
```

```
tcgcaggtgc cggcaccaag gagattgctg tcaccgagct tgacatcgct ggcgccagct    1200
cgaccgacta cgtggaggta agtcgcgaca agccaagtac atagtgtgat taactgatac    1260
caattctcca aatctacagg tcgtcgaagc ctgcctgaac cagcccaagt gtatcggtat    1320
caccgtttgg ggagttgctg acccggtaat taccccctgca gtccggatga tgtcttgcct    1380
taaaacatga gctaatttca atcaggattc ctggcgctcc agctccactc tctgctgtt    1440 cgacagcaac tacaacccga agcctgcata cactgctatc gcaaatgctc tctag         1495
```

<210> SEQ ID NO 6
<211> LENGTH: 417
<212> TYPE: PRT
<213> ORGANISM: Bacillus subtilis

<400> SEQUENCE: 6

```
Met Lys Lys Pro Leu Gly Lys Ile Val Ala Ser Thr Ala Leu Leu Ile
1               5                   10                  15

Ser Val Ala Phe Ser Ser Ile Ala Ser Ala Ser Asp Val Thr
            20                  25                  30

Val Asn Val Ser Ala Glu Lys Gln Val Ile Arg Gly Phe Gly Gly Met
            35                  40                  45

Asn Trp Pro Ala Trp Ala Gly Asp Leu Thr Ala Ala Gln Arg Glu Thr
    50                  55                  60

Ala Phe Gly Asn Gly Gln Asn Gln Leu Gly Phe Ser Ile Leu Arg Ile
65                  70                  75                  80

His Val Asp Glu Asn Arg Asn Asn Trp Tyr Lys Glu Val Glu Thr Ala
                85                  90                  95

Lys Ser Ala Leu Lys Leu Gly Ala Ile Val Phe Ala Ser Pro Trp Asn
            100                 105                 110

Pro Pro Ser Asp Met Val Glu Thr Phe Asn Arg Asn Gly Asp Thr Ser
            115                 120                 125

Ala Lys Arg Leu Lys Tyr Asn Lys Tyr Ala Ala Tyr Ala Gln His Leu
    130                 135                 140

Asn Asp Phe Val Thr Phe Met Lys Asn Asn Gly Val Asn Leu Tyr Ala
145                 150                 155                 160

Ile Ser Val Gln Asn Glu Pro Asp Tyr Ala His Glu Trp Thr Trp Trp
                165                 170                 175

Thr Pro Gln Glu Met Leu Arg Phe Met Arg Glu Asn Ala Gly Ser Ile
            180                 185                 190

Asn Ala Arg Val Ile Ala Pro Glu Ser Phe Gln Tyr Leu Lys Asn Leu
            195                 200                 205

Ser Asp Pro Ile Leu Asn Asp Pro Gln Ala Leu Ala Asn Met Asp Ile
    210                 215                 220

Leu Gly Thr His Leu Tyr Gly Thr Gln Leu Ser Gln Phe Pro Tyr Pro
225                 230                 235                 240

Leu Phe Lys Gln Lys Gly Ala Gly Lys Asp Leu Trp Met Thr Glu Val
                245                 250                 255

Tyr Tyr Pro Asn Ser Asp Thr Asn Ser Ala Asp Arg Trp Pro Glu Ala
            260                 265                 270

Leu Asp Val Ser Gln His Ile His Asn Ala Met Val Glu Gly Asp Phe
            275                 280                 285

Gln Ala Tyr Val Trp Trp Tyr Ile Arg Arg Ser Tyr Gly Pro Met Lys
    290                 295                 300

Glu Asp Gly Thr Ile Ser Lys Arg Gly Tyr Asn Met Ala His Phe Ser
```

-continued

```
            305                 310                 315                 320

Lys Phe Val Arg Pro Gly Tyr Val Arg Ile Asp Ala Thr Lys Asn Pro
                    325                 330                 335

Asn Ala Asn Val Tyr Val Ser Ala Tyr Lys Gly Asp Asn Lys Val Val
                340                 345                 350

Ile Val Ala Ile Asn Lys Ser Asn Thr Gly Val Asn Gln Asn Phe Val
                355                 360                 365

Leu Gln Asn Gly Ser Ala Ser Asn Val Ser Arg Trp Ile Thr Ser Ser
            370                 375                 380

Ser Ser Asn Leu Gln Pro Gly Thr Asn Leu Thr Val Ser Gly Asn His
385                 390                 395                 400

Phe Trp Ala His Leu Pro Ala Gln Ser Val Thr Thr Phe Val Val Asn
                405                 410                 415

Arg
```

LIQUID FORMATION COMPRISING GH10 XYLANASE AND GH62 ARABINOFURANOSIDASE

CROSS-REFERENCE TO RELATED APPLICATIONS

This application is a continuation of U.S. application Ser. No. 16/341,214 filed Apr. 11, 2019, now U.S. Pat. No. 11,180,786, which is a 35 U.S.C. 371 national application of international application no. PCT/CN2017/112865 filed Nov. 24, 2017, which claims priority or the benefit under 35 U.S.C. 119 of international application no. PCT/CN2016/107281 filed Nov. 25, 2016. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to an improved process of treating crop kernels to provide a starch product of high quality suitable for conversion of starch into mono- and oligosaccharides, ethanol, sweeteners, etc. The present invention relates to polypeptides having GH10 xylanase activity and polypeptides having GH62 arabinofuranosidase activity. The present invention also relates to a process for extraction or separation of crude palm oil. Further, the invention also relates to an enzyme composition comprising one or more enzyme activities suitable for the process of the invention.

Description of the Related Art

Wet milling is often used for separating corn kernels into its four basic components: starch, germ, fiber and protein.

Typically, wet milling processes comprise four basic steps. First the kernels are soaked or steeped for about 30 minutes to about 48 hours to begin breaking the starch and protein bonds. The next step in the process involves a coarse grind to break the pericarp and separate the germ from the rest of the kernel. The remaining slurry consisting of fiber, starch and protein is finely ground and screened to separate the fiber from the starch and protein. The starch is separated from the remaining slurry in hydrocyclones. The starch then can be converted to syrup or alcohol, or dried and sold as corn starch or chemically or physically modified to produce modified corn starch.

The use of enzymes has been suggested for the steeping step of wet milling processes. The commercial enzyme product Steepzyme® (available from Novozymes A/S) has been shown suitable for the first step in wet milling processes, i.e., the steeping step where corn kernels are soaked in water.

More recently, "enzymatic milling", a modified wet-milling process that uses proteases to significantly reduce the total processing time during corn wet milling and eliminates the need for sulfur dioxide as a processing agent, has been developed. Johnston et al., *Cereal Chem*, 81, p. 626-632 (2004).

U.S. Pat. No. 6,566,125 discloses a method for obtaining starch from maize involving soaking maize kernels in water to produce soaked maize kernels, grinding the soaked maize kernels to produce a ground maize slurry, and incubating the ground maize slurry with enzyme (e.g., protease).

U.S. Pat. No. 5,066,218 discloses a method of milling grain, especially corn, comprising cleaning the grain, steeping the grain in water to soften it, and then milling the grain with a cellulase enzyme.

WO 2002/000731 discloses a process of treating crop kernels, comprising soaking the kernels in water for 1-12 hours, wet milling the soaked kernels and treating the kernels with one or more enzymes including an acidic protease.

WO 2002/000911 discloses a process of starch gluten separation, comprising subjecting mill starch to an acidic protease.

WO 2002/002644 discloses a process of washing a starch slurry obtained from the starch gluten separation step of a milling process, comprising washing the starch slurry with an aqueous solution comprising an effective amount of acidic protease.

Palm oil is an edible vegetable oil which is obtained from the mesocarp of palm fruits. Palm fruits or fruitlets grow in large bunches. The palm fruitlets are stripped from the fruit bunches after being sterilized. The high temperature causes the enzymes naturally occurring enzymes in the palm fruits to denature and facilitates stripping of the fruits from the bunch stalks. The palm fruitlets are discharged into vessels commonly referred to as digesters, whereby a digested mash of palm fruits are produced under controlled temperature. The digested mash is then pressed, e.g. by using a screw press for subsequent recovery of palm oil. The crude palm oil may be subjected to screening, e.g. to remove coarse fibers, and then to a clarification process to separate oil from water, cell debris and any remaining fibrous material.

Palm fruit mesocarp contains large amounts of oil present as oil droplets within the mesocarp cells. Generally, the oil extraction rate (OER), which is a measure of the amount of extracted oil relative to the weight of the palm fruits is within the range of 20-24%, depending e.g. on fruit quality, and is subject to seasonal variation. In general, the palm oil milling process has been carefully optimized at each mill to minimize oil losses to the extent possible but there is still a strong incentive to improve the OER.

WO 2012/011130 discloses an enzyme composition (with exocellulolytic, pectinolytic, mammanolytic and glucanoloytic activity) used in a process for palm oil extraction.

There remains a need for improvement of processes for wet milling or palm oil extraction.

SUMMARY OF THE INVENTION

The invention provides a process for treating crop kernels, comprising the steps of: a) soaking kernels in water to produce soaked kernels; b) grinding the soaked kernels; c) and treating the soaked kernels or a fraction of said corn kernels in the presence of an effective amount of a polypeptide having GH62 arabinofuranosidase activity and/or a polypeptide having GH10 xylanase activity; wherein step c) is performed before, during or after step b).

In one embodiment, the process of the present invention further comprising fiber washing step.

In one embodiment, the process of the present invention further comprising starch gluten separation step and starch washing step.

In one embodiment, the invention provides a process mentioned above wherein step c) is performed during fiber washing step.

In one embodiment, the invention provides a process mentioned above wherein the soaking is performed in the presence of between 0.01-1%, preferably 0.05-0.3%, especially 0.1% SO$_2$ and/or NaHSO$_3$.

In one embodiment, the invention provides a process mentioned above wherein the crop kernels are from corn (maize), rice, barley, sorghum bean, or fruit hulls, or wheat.

In one embodiment, the invention provides a process mentioned above further comprising treating the soaked crop kernels or a fraction of said crop kernels in the presence of one or more cellulolytic enzyme(s), preferably the one or more hydrolytic enzymes is expressed in an organism, such as *Trichoderma reesei*.

In one embodiment, the invention provides a process mentioned above wherein said corp kernels or a fraction of said crop kernels is admixed with said one or more hydrolytic enzymes, preferably the one or more hydrolytic enzymes is expressed in an organism, such as *Trichoderma reesei*.

In one embodiment, the invention provides a process mentioned above wherein comprising treating the soaked crop kernels or a fraction of said crop kernels in the presence of a polypeptide having GH30 xylanase activity.

In one embodiment, the invention provides a process mentioned above further comprising treating the soaked crop kernels or a fraction of said crop kernels in the presence of an enzyme selected from the group consisting of a cellulolytic enzyme or a cellulase, an endoglucanase, a protease, a cellobiohydrolase I, a cellobiohydrolase II, a GH61 polypeptide, or a combination thereof.

In one embodiment, the invention provides a process mentioned above wherein the GH62 polypeptide having arabinofuranosidase activity is derived from a strain of genus *Aspergillus*, such as a strain of *Aspergillus niger*.

In one embodiment, the invention provides a process mentioned above wherein the polypeptide having GH62 arabinofuranosidase activity is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 1 or the mature polypeptide of SEQ ID NO: 3;
(b) a variant of the mature polypeptide of SEQ ID NO: 1 or the mature polypeptide of SEQ ID NO: 3 comprising a substitution, deletion, and/or insertion at one or more (several) positions.

In one embodiment, the invention provides a process mentioned above wherein the polypeptide having GH10 xylanase activity is derived from a strain of the genus *Aspergillus*, such as a strain of *Aspergillus niger*.

In one embodiment, the invention provides a process mentioned above wherein the polypeptide having GH10 xylanase activity is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 4;
(b) a variant of the mature polypeptide of SEQ ID NO: 4 comprising a substitution, deletion, and/or insertion at one or more (several) positions.

In one embodiment, the invention provides a process mentioned above wherein the polypeptide having GH30 xylanase activity is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 6;
(b) a variant of the mature polypeptide of SEQ ID NO: 6 comprising a substitution, deletion, and/or insertion at one or more (several) positions.

In one embodiment, the invention provides a process mentioned above wherein the polypeptide having GH30 xylanase activity is derived from a strain of the genus *Bacillus*, such as a strain of *Bacillus subtilis*.

In one embodiment, the invention provides a process mentioned above wherein the fiber washing step comprise a space configured to provide a total retention time in the fiber washing system of at least 0.5 hour, preferably at least 2 hours, most preferably at least 4 hours.

The invention also provides a polypeptide having GH62 arabinofuranosidase activity, selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 1;
(b) a variant of the mature polypeptide of SEQ ID NO: 1 comprising a substitution, deletion, and/or insertion at one or more (several) positions;
(c) a polypeptide encoded by a polynucleotide having at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 2 or the cDNA sequence thereof.

In one embodiment, the polypeptide having GH62 arabinofuranosidase activity of the invention is derived from a strain of the genus *Aspergillus*, such as a strain of *Aspergillus niger*.

The invention also provides a polypeptide having GH10 xylanase activity, selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 4;
(b) a variant of the mature polypeptide of SEQ ID NO: 4 comprising a substitution, deletion, and/or insertion at one or more (several) positions;
(c) a polypeptide encoded by a polynucleotide having at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof.

In one embodiment, the polypeptide having GH10 xylanase activity of the invention is derived from a strain of the genus *Aspergillus*, such as a strain of *Aspergillus niger*.

The invention also provides a process for extraction or separation of crude palm oil, comprising the steps of: contacting a substrate comprising palm oil with an enzyme composition, extracting or separating the crude palm oil; wherein the enzyme composition comprises a GH10 xylanase and a GH62 arabinofuranosidase.

In one embodiment, the GH10 xylanase of the present invention and the GH62 arabinofuranosidase of the present invention are defined in any one of the preceding embodiments.

The invention also provides a use of a polypeptide having GH62 arabinofuranosidase activity, a polypeptide having GH10 xylanase activity, or a polypeptide having GH30 xylanase activity, to improve the total starch yield and/or gluten yield from corn kernels in a process as defined in any one of the preceding embodiments or to improve oil yield from crude palm oil in a process defined in any one of the preceding embodiments, wherein, preferably the said polypeptides are defined in any one of the preceding embodiments.

The invention also provides an enzyme composition comprising or consisting of a GH62 arabinofuranosidase, a GH10 xylanase, and/or a GH30 xylanase, preferably, the GH62 arabinofuranosidase, the GH10 xylanase and/or the GH30 xylanase is defined in any one of the preceding embodiments.

In one embodiment, the enzyme composition of the present invention further comprising of one or more hydrolytic enzymes, preferably one or more cellulolytic enzyme, preferably, the one or more cellulolytic enzymes is expressed in an organism, such as *Trichoderma reesei*.

DEFINITIONS

Arabinofuranosidase: The term "arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,2)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, CA, USA).

The arabinofuranosidase of the present invention have at least at least 20%, e.g., at least 40%, at least 50%, at least 60%, at least 70%, at least 80%, at least 90%, at least 95%, or at least 100% of the arabinofuranosidase activity of one or more of the polypeptides selected from the list consisting of SEQ ID NO: 1 and SEQ ID NO: 3.

Arabinoxylan-containing material: The term "Arabinoxylan-containing material" means any material containing arabinoxylan. Arabinoxylan is a hemicellulose found in both the primary and secondary cell walls of plants, including woods and cereal grains, consisting of copolymers of two pentose sugars, arabinose and xylose. The arabinoxylan chain contains a large number of 1,4-linked xylose units. Many xylose units are substituted with 2-, 3- or 2,3-substituted arabinose residues.

Examples of arabinoxylan-containing material are forage, roughage, seeds and grains (either whole or prepared by crushing, milling, etc from e.g. corn, oats, rye, barley, wheat), trees or hard woods (such as poplar, willow, eucalyptus, palm, maple, birch), bamboo, herbaceous and/or woody energy crops, agricultural food and feed crops, animal feed products, cassava peels, cocoa pods, sugar cane, sugar beet, locust bean pulp, vegetable or fruit pomaces, wood waste, bark, shavings, sawdust, wood pulp, pulping liquor, waste paper, cardboard, construction and demolition wood waste, industrial or municipal waste water solids or sludge, manure, by-product from brewing and/or fermentation processes, wet distillers grain, dried distillers grain, spent grain, vinasse and bagasse.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (Lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, miscanthus, orchard grass, ryegrass, switchgrass, Timothy-grass), corn (maize), hemp, millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Preferred sources of arabinoxylan-containing materials are forage, roughage, seeds and grains, sugar cane, sugar beet and wood pulp.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Xylanase: The term "xylanase" means a 1,4-beta-D-xylan-xylohydrolase (E.C. 3.2.1.8) that catalyses the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

In one aspect, the GH10 xylanase of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO:4.

In one aspect, the GH30 xylanase of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO: 6.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teen et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Cellulosic material: The term "cellulosic material" means any material containing cellulose. Cellulose is a homopolymer of anyhdrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Crop kernels: The term "crop kernels" includes kernels from, e.g., corn (maize), rice, barley, sorghum bean, fruit hulls, and wheat. Corn kernels are exemplary. A variety of corn kernels are known, including, e.g., dent corn, flint corn, pod corn, striped maize, sweet corn, waxy corn and the like. In an embodiment, the corn kernel is yellow dent corn kernel. Yellow dent corn kernel has an outer covering referred to as the "Pericarp" that protects the germ in the kernels. It resists water and water vapour and is undesirable to insects and microorganisms. The only area of the kernels not covered by the "Pericarp" is the "Tip Cap", which is the attachment point of the kernel to the cob.

Dry solids: The term "dry solids" is the total solids of a slurry in percent on a dry weight basis.

Endoglucanase: The term "endoglucanase" means a 4-(1, 3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Protease: The term "proteolytic enzyme" or "protease" means one or more (e.g., several) enzymes that break down the amide bond of a protein by hydrolysis of the peptide bonds that link amino acids together in a polypeptide chain. A protease may include, e.g., a metalloprotease, a trypsin-like serine protease, a subtilisin-like serine protease, and aspartic protease.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide, wherein the fragment has enzyme activity. In one aspect, a fragment contains at least 85%, e.g., at least 90% or at least 95% of the amino acid residues of the mature polypeptide of an enzyme.

Germ: The "Germ" is the only living part of the corn kernel. It contains the essential genetic information, enzymes, vitamins, and minerals for the kernel to grow into a corn plant. In yellow dent corn, about 25 percent of the germ is corn oil. The endosperm covered or surrounded by the germ comprises about 82 percent of the kernel dry weight and is the source of energy (starch) and protein for the germinating seed. There are two types of endosperm, soft and hard. In the hard endosperm, starch is packed tightly together. In the soft endosperm, the starch is loose.

Grind or grinding: The term "grinding" means any process that breaks the pericarp and opens the crop kernel.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Milled: The term "milled" refers to plant material which has been broken down into smaller particles, e.g., by crushing, fractionating, grinding, pulverizing, etc.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide of SEQ ID NO: 1 consists of amino acids 27 to 332, amino acids 1 to 26 of SEQ ID NO: 1 being a signal peptide.

In one aspect, the mature polypeptide of SEQ ID NO: 3 consists of amino acids 27 to 332, amino acids 1 to 26 of SEQ ID NO: 3 being a signal peptide.

In one aspect, the mature polypeptide of SEQ ID NO: 4 consists of amino acids 20 to 319, amino acids 1 to 19 of SEQ ID NO: 4 being a signal peptide.

In one aspect, the mature polypeptide of SEQ ID NO: 6 consists of amino acids 27 to 417, amino acids 1 to 26 of SEQ ID NO: 6 being a signal peptide.

Mature polypeptide coding sequence: The term "mature polypeptide coding sequence" means a polynucleotide that encodes a mature polypeptide.

In one aspect, the mature polypeptide coding sequence of a GH62 arabinofuranosidase is nucleotides 79 to 996 of SEQ ID NO: 2 or the cDNA sequence thereof.

In another aspect, the mature polypeptide coding sequence of a GH10 xylanase is nucleotides 58 to 244,301 to 341,401 to 449,511 to 632,685 to 830,884 to 972,1029 to 1052,1129 to 1217,1280 to 1345,1406 to 1492 of SEQ ID NO: 5 or the cDNA sequence thereof.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Oligosaccharide: The term "oligosaccharide" is a compound having 2 to 10 monosaccharide units.

Operably linked: The term "operably linked" means a configuration in which a control sequence is placed at an appropriate position relative to the coding sequence of a polynucleotide such that the control sequence directs expression of the coding sequence.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows:

(Identical Residues×100)/(Length of Alignment–Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the –nobrief option) is used as the percent identity and is calculated as follows:

(Identical Deoxyribonucleotides×100)/(Length of Alignment–Total Number of Gaps in Alignment)

Starch: The term "starch" means any material comprised of complex polysaccharides of plants, composed of glucose units that occurs widely in plant tissues in the form of storage granules, consisting of amylose and amylopectin, and represented as $(C_6H_{10}O_5)_n$, where n is any number.

Steep or steeping: The term "steeping" means soaking the crop kernel with water and optionally $SO_2$.

Subsequence: The term "subsequence" means a polynucleotide having one or more (e.g., several) nucleotides absent from the 5' and/or 3' end of a mature polypeptide coding sequence; wherein the subsequence encodes a fragment having arabinofuranosidase or xylanase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having xylanase or arabinofuranosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Wet milling benefit: The term "wet milling benefit" means one or more of improved starch yield and/or purity, improved gluten quality and/or yield, improved fiber, gluten, or steep water filtration, dewatering and evaporation, easier germ separation and/or better post-saccharification filtration, and process energy savings thereof.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, MO, USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Crude oil: The term "crude oil" (also called a non-degummed oil) refers to a pressed or extracted oil or a mixture thereof. In the present context, it is to be understood that the oil is palm oil, in particular un-refined palm oil. In particular, the term "crude oil" refers to the effluent from the screw press of a palm oil mill; i.e. to the mixture of oil and water pressed out of the palm fruit mash, before it has been subject to clarification and separation of oil from water. The crude palm oil is also designated CPO. Crude palm oil comprises water.

Digestion: The term "digestion" refers to a process where the substrate comprising palm oil is kept at a temperature in the range of 65-85° C. for disintegrating the substrate and releasing palm oil from the mesocarp. The digestion can be carried out in a digestion tank and/or a precooker tank equipped with baffles. During the digestion, the substrate comprising palm oil e.g. the palm fruitlets are disintegrated and oil released from the mesocarp. According to the invention the substrate comprising palm oil can be contacted with the enzyme composition before or during the digestion.

Oil extraction rate (OER): "Oil extraction rate (OER)" may be defined as by Chang et al., oil palm Industry economic journal, volume 3, 2003[9]. Chang et al. defines the Oil extract rate as ratio of oil recovered and Fresh fruit branch (FFB) times 100, the mathematical formula is:

OER=(weight of oil recovered/weight of FFB processed)×100

Palm oil mill effluent (POME): Palm oil mill effluent (POME) is the waste water discharged e.g. from the sterilization process, crude oil clarification process.

Palm press liquid: The term "palm press liquid" refers to the liquid discharged from the pressing of the substrate comprising palm oil. Palm press liquid is not a crude palm oil and water has not been separated from the palm press liquid.

Nomenclature

For purposes of the present invention, the nomenclature [Y/F] means that the amino acid at this position may be a tyrosine (Try, Y) or a phenylalanine (Phe, F). Likewise the nomenclature [V/G/A/l] means that the amino acid at this position may be a valine (Val, V), glycine (Gly, G), alanine (Ala, A) or isoleucine (lie, I), and so forth for other combinations as described herein. Unless otherwise limited further, the amino acid X is defined such that it may be any of the 20 natural amino acids.

DETAILED DESCRIPTION OF THE INVENTION

Milling Process

It is an object of the invention to provide improved processes of treating crop kernels to provide starch of high quality.

In one embodiment, the enzyme compositions useful in the processes of the invention provide benefits including, improving starch yield and/or purity, improving gluten quality and/or yield, improving fiber, gluten, or steep water filtration, dewatering and evaporation, easier germ separation and/or better post-saccharification filtration, and process energy savings thereof.

Moreover, the present inventors have surprisingly found that the enzymes useful according to the invention provide reduction in fiber mass and lower protein content of the fiber due to better separation of both starch and protein fractions from the fiber fraction. Separating starch and gluten from fiber is valuable to the industry because fiber is the least valuable product of the wet milling process, and higher purity starch and protein is desirable.

Surprisingly, the present inventors have discovered that replacing some of the protease activity in an enzyme composition can provide an improvement over an otherwise similar composition containing predominantly protease activity alone. This can provide a benefit to the industry, e.g., on the basis of cost and ease of use.

The kernels are milled in order to open up the structure and to allow further processing and to separate the kernels into the four main constituents: starch, germ, fiber and protein.

In one embodiment, a wet milling process is used. Wet milling gives a very good separation of germ and meal (starch granules and protein) and is often applied at locations where there is a parallel production of syrups.

The inventors of the present invention have surprisingly found that the quality of the starch final product may be improved by treating crop kernels in the processes as described herein.

The processes of the invention result in comparison to traditional processes in a higher starch quality, in that the final starch product is more pure and/or a higher yield is obtained and/or less process time is used. Another advantage may be that the amount of chemicals, such as SO2 and NaHSO3, which need to be used, may be reduced or even fully removed.

Wet Milling

Starch is formed within plant cells as tiny granules insoluble in water. When put in cold water, the starch granules may absorb a small amount of the liquid and swell. At temperatures up to about 50° C. to 75° C. the swelling may be reversible. However, with higher temperatures an irreversible swelling called "gelatinization" begins. Granular starch to be processed according to the present invention may be a crude starch-containing material comprising (e.g., milled) whole grains including non-starch fractions such as germ residues and fibers. The raw material, such as whole grains, may be reduced in particle size, e.g., by wet milling, in order to open up the structure and allowing for further processing. Wet milling gives a good separation of germ and meal (starch granules and protein) and is often applied at locations where the starch hydrolyzate is used in the production of, e.g., syrups.

In an embodiment, the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

More particularly, degradation of the kernels of corn and other crop kernels into starch suitable for conversion of starch into mono- and oligo-saccharides, ethanol, sweeteners, etc. consists essentially of four steps:
1. Steeping and germ separation,
2. Fiber washing and drying,
3. Starch gluten separation, and
4. Starch washing.

1. Steeping and Germ Separation

Corn kernels are softened by soaking in water for between about 30 minutes to about 48 hours, preferably 30 minutes to about 15 hours, such as about 1 hour to about 6 hours at a temperature of about 50° C., such as between about 45° C. to 60° C. During steeping, the kernels absorb water, increasing their moisture levels from 15 percent to 45 percent and more than doubling in size. The optional addition of e.g. 0.1 percent sulfur dioxide (SO2) and/or NaHSO3 to the water prevents excessive bacteria growth in the warm environment. As the corn swells and softens, the mild acidity of the steepwater begins to loosen the gluten bonds within the corn and release the starch. After the corn kernels are steeped they are cracked open to release the germ. The germ contains the valuable corn oil. The germ is separated from the heavier density mixture of starch, hulls and fiber essentially by "floating" the germ segment free of the other substances under closely controlled conditions. This method serves to eliminate any adverse effect of traces of corn oil in later processing steps.

In an embodiment of the invention the kernels are soaked in water for 2-10 hours, preferably about 3-5 hours at a temperature in the range between 4° and 60° C., preferably around 50° C.

In one embodiment, 0.01-1%, preferably 0.05-0.3%, especially 0.1% $SO_2$ and/or $NaHSO_3$ may be added during soaking.

2. Fiber Washing and Drying

To get maximum starch recovery, while keeping any fiber in the final product to an absolute minimum, it is necessary to wash the free starch from the fiber during processing. The fiber is collected, slurried and screened to reclaim any residual starch or protein.

3. Starch Gluten Separation

The starch-gluten suspension from the fiber-washing step, called mill starch, is separated into starch and gluten. Gluten has a low density compared to starch. By passing mill starch through a centrifuge, the gluten is readily spun out.

4. Starch Washing

The starch slurry from the starch separation step contains some insoluble protein and much of solubles. They have to be removed before a top quality starch (high purity starch) can be made. The starch, with just one or two percent protein remaining, is diluted, washed 8 to 14 times, re-diluted and washed again in hydroclones to remove the last trace of protein and produce high quality starch, typically more than 99.5% pure.

Products

Wet milling can be used to produce, without limitation, corn steep liquor, corn gluten feed, germ, corn oil, corn gluten meal, corn starch, modified corn starch, syrups such as corn syrup, and corn ethanol.

Palm Oil Extraction

The present invention also provides a process for enzyme assisted extraction of crude palm oil from a substrate comprising palm oil. The substrate comprising palm oil can be selected from the group consisting of palm fruitlets, pressed palm fruit liquid, mashed or partly mashed palm fruitlets. The inventors have found that by using a GH10 xylanase on the substrate comprising palm oil, the oil extraction rate (OER) can be increased.

The invention concerns a process for extraction or separation of crude palm oil (CPO), comprising the steps of:
i) contacting a substrate comprising palm oil with an enzyme composition,
ii) extracting or separating the crude palm oil (CPO)
wherein the enzyme composition comprises a GH10 xylanase and a GH62 arabinofuranosidase.

In one embodiment of the invention, the substrate comprising palm oil is palm fruitlets, which comprise oil in the mesocarp of the fruit. The palm fruitlets are contacted with the enzyme composition. In one embodiment, the substrate is palm fruitlets, which are mashed or partly mashed and contacted with the enzyme composition. This increases availability of mesocarp cells and thereby enhances enzyme activity on the mesocarp cells. In one embodiment, the substrate comprising palm oil is crude palm oil which is contacted with the enzyme composition. In the various aspects and embodiments of the invention the substrate, which comprises palm oil may be a substrate which also comprises fiber, in particular fiber from the mescocarp of palm fruitlets.

In one embodiment of the invention the substrate comprising palm oil is sterilized before being contacted with the enzyme composition. Palm fruits grow in large bunches and needs to be stripped from the bunch stalks before being contacted with the enzyme composition. Steam sterilization of the fresh fruit bunches facilitates fruits being stripped from bunches to give the palm fruitlet. The sterilization step has several advantages one being that it softens the fruit mesocarp for subsequent digestion. A further advantage is that the quality of the final palm oil product is better if the palm fruits are stripped from the bunch stalks.

The sterilization can be a batch sterilization or a continuous sterilization. The sterilization process can be carried out at a temperature of 100° C.-150° C. In one embodiment of the invention, the pressure is reduced during the sterilization procedure.

After the sterilization, the palm fruitlets are stripped from the bunch stalks. Stripping or threshing can be carried out in a mechanized system having a rotating drum or fixed drum equipped with rotary beater bars which detach the fruit from the bunch and leaves the spikelets on the stem. The stripped palm fruitlets can be contacted with the enzyme composition according to the invention.

In one embodiment of the invention, the substrate comprising palm oil is subjected to digestion before extracting the crude palm oil. The stripped palm fruitlets can be transported into a digester by one or more transportation means, e.g. a conveyor belt. In the digester, the fruitlets are further heated in order to loosen the pericarp. The digester is typically a steam heated vessel, which has rotating shafts to which stirring arms are attached or is equipped with baffles. The fruitlets are rotated, causing the loosening of the pericarps from the nuts and degradation of the mesocarp. The digester is a continuous process where the digester is kept full and as the digested fruit is drawn out, freshly stripped fruits are brought in.

In one embodiment of the invention, the first part of the digestion is carried out in a precooker. The substrate may be held at a temperature within the range of 65-85° C. for some time and then transferred to the digester tank.

Polypeptides Having GH62 Arabinofuranosidase Activity

Preferred embodiments of the aspect of the invention relating to the GH62 polypeptide having arabinofuranosidase activity are disclosed herein below.

In an embodiment, the polypeptide having GH62 arabinofuranosidase activity of the present invention, is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 1;
(b) a variant of the mature polypeptide of SEQ ID NO: 1 comprising a substitution, deletion, and/or insertion at one or more (several) positions;
(c) a polypeptide encoded by a polynucleotide having at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 2 or the cDNA sequence thereof.

In an embodiment, the polypeptide having GH62 arabinofuranosidase activity of the present invention, is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 3;
(b) a variant of the mature polypeptide of SEQ ID NO: 3 comprising a substitution, deletion, and/or insertion at one or more (several) positions.

In one aspect, the polypeptide differs by up to 10 amino acids, e.g., 1, 2, 3, 4, 5, 6, 7, 8, 9, or 10, from the mature polypeptide. In another embodiment, the present invention relates to variants of the mature polypeptide comprising a substitution, deletion, and/or insertion at one or more (e.g., several) positions. In an embodiment, the number of amino acid substitutions, deletions and/or insertions introduced into the mature polypeptide is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

A polypeptide having arabinofuranosidase activity may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one embodiment, the polypeptide is from a fungus of the order Eurotiales, or from the family Aspergillaceae, or from the genus Aspergillus or from the species Aspergillus clavatus or Aspergillus wentii or Aspergillus niger.

In one embodiment, the GH62 arabinofuranosidase is derived from a strain of the genus Aspergillus, such as a strain of Aspergillus niger.

In one embodiment, the polypeptide is from a fungus of the order Eurotiales, or from the family Aspergillaceae, or from the genus Neosartorya or from the species Neosartorya fischeri.

In one embodiment, the polypeptide is from a fungus of the order Eurotiales, or from the family Trichocomaceae, or from the genus Talaromyces or from the species Talaromyces pinophilus.

The polypeptide may be a bacterial polypeptide. In one embodiment, the polypeptide is from a bacterium of the order Actinomycetales, or from the family Streptomycetaceae, or from the genus Streptomyces or from the species Streptomyces nitrosporeus or Streptomyces beijiangensis.

In one embodiment, the polypeptide is from a bacterium of the order Actinomycetales, or from the family Streptosporangiaceae, or from the genus Streptosporangium or from the species Streptosporangium sp-60756.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polypeptides Having GH10 Xylanase Activity

Exemplary embodiments relating to the GH10 polypeptide having xylanase activity are disclosed herein below.

In an embodiment, the polypeptide having GH10 xylanase activity, selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 4;
(b) a variant of the mature polypeptide of SEQ ID NO: 4 comprising a substitution, deletion, and/or insertion at one or more (several) positions;
(c) a polypeptide encoded by a polynucleotide having at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof.

In one aspect, the polypeptide differs by up to 10 amino acids, e.g., 1, 2, 3, 4, 5, 6, 7, 8, 9, or 10, from the mature polypeptide. In another embodiment, the present invention relates to variants of the mature polypeptide comprising a substitution, deletion, and/or insertion at one or more (e.g., several) positions. In an embodiment, the number of amino acid substitutions, deletions and/or insertions introduced into the mature polypeptide is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

A polypeptide having xylanase activity of the present invention (GH10 xylanase) may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Talaromyces* polypeptide.

In another embodiment, the polypeptide is a *Talaromyces leycettanus* polypeptide, e.g., a polypeptide obtained from *Talaromyces leycettanus* Strain CBS398.68.

The polypeptide may be an *Aspergillus* polypeptide. In another embodiment, the polypeptide is an *Aspergillus niger* polypeptide, In one embodiment, the GH10 xylanase is derived from a strain of the genus *Aspergillus*, such as a strain of *Aspergillus niger*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polypeptides Having GH30 Xylanase Activity

GH30 polypeptide refers to a polypeptide with enzyme activity, the polypeptide being classified as member of the Glycoside hydrolase family 30 in the database of Carbohydrate-Active enZYmes (CAZymes) (http://www.cazy.org/).

In one embodiment, the polypeptide having GH30 xylanase activity is selected from the group wherein the polypeptide having GH30 xylanase activity is selected from the group consisting of:
(a) a polypeptide having at least 85%, e.g., at least 90%, at least 95%, at least 96%, at least 97%, at least 98%, at least 99% or 100% sequence identity to the mature polypeptide of SEQ ID NO: 6;
(b) a variant of the mature polypeptide of SEQ ID NO: 6 comprising a substitution, deletion, and/or insertion at one or more (several) positions.

In one aspect, the polypeptide differs by up to 10 amino acids, e.g., 1, 2, 3, 4, 5, 6, 7, 8, 9, or 10, from the mature polypeptide. In another embodiment, the present invention relates to variants of the mature polypeptide comprising a substitution, deletion, and/or insertion at one or more (e.g., several) positions. In an embodiment, the number of amino acid substitutions, deletions and/or insertions introduced into the mature polypeptide is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

A polypeptide having xylanase activity of the present invention (GH30 xylanase) may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the polypeptide having GH30 xylanase activity is derived from a strain of the genus *Bacillus*, such as a strain of *Bacillus subtilis*.

The polypeptide may be a bacterial polypeptide. In one embodiment, the polypeptide may be a *Bacillus* polypeptide. In another embodiment, the polypeptide is a *Bacillus subtilis* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Cellulolytic Composition

Exemplary cellulolytic compositions are as described in e.g., WO 2015/081139 and PCT/US2015/034179.

In an embodiment, the cellulolytic composition is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*.

In a preferred embodiment, the cellulolytic composition is derived from a strain of *Trichoderma reesei*.

In a preferred embodiment, the cellulolytic composition is a *Trichoderma reesei* cellulase preparation.

In an embodiment, the cellulolytic composition comprises a *Trichoderma reesei* cellulase preparation containing *Aspergillus oryzae* beta-glucosidase fusion protein (WO 2008/057637) and *Thermoascus aurantiacus* GH61A polypeptide (WO 2005/074656).

In an embodiment, the cellulolytic composition comprises a *Trichoderma reesei* cellulolytic enzyme composition, further comprising *Thermoascus aurantiacus* GH61A polypeptide having cellulolytic enhancing activity (WO 2005/074656) and *Aspergillus oryzae* beta-glucosidase fusion protein (WO 2008/057637).

In another embodiment, the cellulolytic composition comprises a *Trichoderma reesei* cellulolytic enzyme composition, further comprising *Thermoascus aurantiacus* GH61A polypeptide having cellulolytic enhancing activity (Sequence Number 2 in WO 2005/074656) and *Aspergillus fumigatus* beta-glucosidase (Sequence Number 2 of WO 2005/047499).

In another embodiment, the cellulolytic composition comprises a *Trichoderma reesei* cellulolytic enzyme composition, further comprising *Penicillium emersonii* GH61A polypeptide having cellulolytic enhancing activity disclosed in WO 2011/041397, *Aspergillus fumigatus* beta-glucosidase (Sequence Number 2 of WO 2005/047499) or a variant thereof with the following substitutions: F100D, S283G, N456E, F512Y.

In an embodiment, the cellulolytic composition is derived from *Trichoderma reesei* RutC30.

In an embodiment, the cellulolytic composition comprises a *Trichoderma reesei* cellulase preparation containing *Trichophaea saccata* GH10 xylanase (WO 2011/057083) and *Talaromyces emersonii* beta-xylosidase.

Enzyme Composition

The present invention also provides an enzyme composition comprising of a GH62 arabinofuranosidase, a GH10 xylanase, and/or a GH30 xylanase.

In an embodiment, the enzyme composition of the present invention further comprises one or more hydrolytic enzymes, preferably one or more cellulolytic enzyme, preferably, the one or more cellulolytic enzymes is expressed in an organism, such as *Trichoderma reesei*.

In an embodiment, the enzyme composition of the present invention further comprises a cellulolytic composition.

Preferably, the compositions are enriched in the polypeptides useful according to the invention. The term "enriched" indicates that the enzymatic activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10. In an embodiment, the composition comprises the polypeptides of the first aspect of the invention and one or more formulating agents, as described in the 'formulating agent' section below.

The compositions may comprise a polypeptide of the present invention as the major enzymatic component, e.g., a mono-component composition. Such a composition may further comprise a formulating agent, as described in the 'formulating agent' section below. Alternatively, the compositions may comprise multiple enzymatic activities, such as one or more (e.g., several) enzymes selected from the group consisting of phytase, xylanase, galactanase, alpha-galactosidase, protease, phospholipase, glucoronidase, lysophospholipase, amylase, beta-glucanase, arabinofuranosidase, beta-xylosidase, endo-1,4-beta-xylanase acetyl xylan esterase, feruloyl esterase, cellulase, cellobiohydrolase, beta-glycosidase, pullulanase, or any mixture thereof. Additional cellulolytic activities are particularly contemplated, as further outlined below.

Where arabinofuranosidase and xylanase activity are contemplated, it is at present contemplated that the xylanase is used in one or more of the following amounts (dosage ranges): 0.01-200; 0.05-100; 0.1-50; 0.2-20; 0.1-1; 0.2-2; 0.5-5; or 1-10 wherein all these ranges are mg xylanase protein per kg substrate (ppm). It is at present contemplated that the arabinofuranosidase is administered in one or more of the following amounts (dosage ranges): 0.01-200; 0.05-100; 0.1-50; 0.2-20; 0.1-1; 0.2-2; 0.5-5; or 1-10 wherein all these ranges are mg arabinofuranosidase protein per kg substrate (ppm). It is further contemplated that the ratio of the GH10 xylanase to GH62 arabinofuranosidase is in the range of 100:1 to 1:100 xylanase:arabinofuranosidase such as the ranges 50:1 to 1:50, 50:1 to 1:10, 25:1 to 1:5, 10:1 to 1:2 or such as 10:1 to 1:50, 5:1 to 1:25, 2:1 to 1:10 xylanase:arabinofuranosidase.

Formulating Agent

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol.

For a solid formulation, the formulation may be for example as a granule, spray dried powder or agglomerate. The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In an embodiment, the solid composition is in granulated form. The granule may have a matrix structure where the components are mixed homogeneously. However, the granule typically comprises a core particle and one or more coatings, which typically are salt and/or wax coatings. The core particle can either be a homogeneous blend of xylanase of the invention optionally combined with one or more additional enzymes and optionally together with one or more salts or an inert particle with the xylanase of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals.

The salt coating is typically at least 1 µm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

Enzymatic Amount

Enzymes may be added in an effective amount during wet milling process, which can be adjusted according to the practitioner and particular process needs. In general, enzyme may be present in an amount of 0.0001-1 mg enzyme protein per g dry solids (DS) kernels, such as 0.001-0.1 mg enzyme protein per g DS kernels. In particular embodiments, the enzyme may be present in an amount of, e.g., 1 µg, 2.5 µg, 5 µg, 10 µg, 20 µg, 25 µg, 30 µg, 35 µg, 40 µg, 45 µg, 50 µg, 75 µg, 100 µg, 125 µg, 150 µg, 175 µg, 200 µg, 225 µg, 250 µg, 275 µg, 300 µg, 325 µg, 350 µg, 375 µg, 400 µg, 450 µg, 500 µg, 550 µg, 600 µg, 650 µg, 700 µg, 750 µg, 800 µg, 850 µg, 900 µg, 950 µg, 1000 µg enzyme protein per g DS kernels.

In some embodiments of palm oil extraction, the enzyme(s) are dosed at amounts corresponding to 10-1000 ppm, such as 20-1000 ppm, 30-1000 ppm, 40-1000 ppm, 50-1000 ppm, 100-1000 ppm, 200-1000 ppm, 100-500 ppm, such as 200-500 ppm, 250-400 ppm or 350-1000 ppm relative to the amount of substrate comprising palm oil.

The present invention is further described by the following examples that should not be construed as limiting the scope of the invention.

EXAMPLES

Materials and Methods
Enzymes

GH62 Arabinofuranosidase A: GH62 arabinofuranosidase derived from *Aspergillus niger* (SEQ ID NO: 1).

GH62 Arabinofuranosidase B: GH62 arabinofuranosidase derived from *Aspergillus niger* (SEQ ID NO: 3).

GH10 Xylanase A: GH10 xylanase derived from *Aspergillus niger* (SEQ ID NO: 4).

GH30 Xylanase A: GH30 xylanase derived from *Bacillus subtilis* (SEQ ID NO: 6)

Celluclast 1.5 L: a commercial product comprising cellulase and available at Novozymes A/S.

Example 1: Cloning and Recombinant Expression of a GH62 Arabinofuranosidase from *Aspergillus niger*

The arabinofuranosidase encoding gene with SEQ ID NO: 2 was PCR amplified from genomic DNA isolated from an *Aspergillus niger* strain, which was isolated from Ireland, using gene-specific primers that also included a Kozak translation initiation sequence, "CACC", immediately 5' of the start codon. The PCR amplified product was cloned into the *Aspergillus* expression vector pMStr57 (WO 04/032648) that had been digested with the restriction enzymes BamHI and XhoI.

The sequence of the GH62 arabinofuranosidase encoding gene cloned in the expression vector was confirmed, and the expression construct was transformed into the *Aspergillus oryzae* strain MT3568 by the methods described in Christensen et al., 1988, Biotechnology 6, 1419-1422 and WO 04/032648. Transformants were selected during regeneration from protoplasts based on the ability to utilize acetamide as a nitrogen source conferred by a selectable marker in the expression vector. Production of the recombinant arabinofuranosidase was evaluated by culturing the transformants in 96-well deep-well microtiter plates for 4 days at 30° C. in YPG medium (WO 05/066338) and monitoring arabinofuranosidase expression by SDS-PAGE. The transformant showing the highest level of expression in microtiter plate culture was selected and re-isolated twice under selection.

For larger-scale production of the recombinant arabinofuranosidase, the selected transformant was cultured in 500 ml baffled flasks containing 150 ml of DAP-4C-1 medium (WO 12/103350). The cultures were shaken on a rotary table at 150 RPM at for 4 days. The culture broth was subsequently separated from cellular material by passage through a 0.22 µm filtration unit.

Example 2: Chromatographic Purification of the Recombinant Arabinofuranosidase from *Aspergillus niger* pH of the filtered sample was adjusted to around pH 7.5 and 1.8M ammonium sulfate was added. The sample was applied to a 5 ml HiTrap™ Phenyl (HS) column on an Åkta Explorer. Prior to loading, the column had been equilibrated in 5 column volumes (CV) of 50 mM HEPES+1.8M AMS (ammonium sulfate) pH 7. In order to remove unbound material, the column was washed with 5 CV of 50 mM HEPES+1.8M AMS pH 7. The target protein was eluted from the column into a 10 ml loop using 50 mM HEPES+ 20% isopropanol pH 7. From the loop, the sample was loaded onto a desalting column (HiPrep™ 26/10 Desalting), which had been equilibrated with 3 CV of 50 mM HEPES+ 100 mM NaCl pH 7.0. The target protein was eluted with 50 mM HEPES+100 mM NaCl pH 7.0 and relevant fractions were selected and pooled based on the chromatogram. The flow rate was 5 ml/min.

The GH62 arabinofuranosidase coding sequence and the full-length amino acid sequence of the GH62 arabinofuranosidase are shown in SEQ ID NO: 1 and SEQ ID NO: 2, respectively. Determination of the N-terminal sequence was: KCSLPSS, which was determined by N-terminal Edman degradation Sequencing.

Example 3: Genomic DNA Extraction from *Aspergillus niger* NN053297

The *Aspergillus niger* strain NN053297 was isolated from hot spring soil samples collected from Yunnan province in 2010.

*Aspergillus niger* strain NN053297 was inoculated on PDA plate and incubated for 37 C for 4 days. Mycelia were collected and frozen in liquid nitrogen in a sterilized mortar and grounded with pestle to fine powders. Then the genomic DNA was extracted with Biospin Fungus Genomic DNA Extraction Kit (Bioer Technology Co. Ltd., Hangzhou, China) following the manufacturer's instruction.

Example 4: Cloning of *Aspergillus niger* GH10 Xylanase Gene into an *Aspergillus oryzae* Expression Vector Based on the DNA information from public database, oligonucleotide primers, shown below, were designed to amplify the coding sequence of the *Aspergillus niger* GH10 xylanase. The GH10 xylanase coding sequence and the full-length amino acid sequence are shown as SEQ ID NO: 5 & SEQ ID NO: 4. The primers were synthesized by Invitrogen, Beijing, China.

```
primer1     ACACAACTGGGGATCCACCatggttc
            agatcaaggtagctgcac
primer2     CCCTCTAGATCTCGAGctagagagca
            tttgcgatagcagtgta
```

Lowercase characters of primer1 and primer2 represent the coding region the gene. While bold characters represent a region homologous to insertion sites of *Aspergillus oryzae* expression vector pCaHj505 as described in WO2013029496. The 4 underlined letters in primer1 represent the Kozark sequence as the initiation of translation process.

The genomic DNA was prepared in Example 1. A Phusion™ High-Fidelity DNA Polymerase (Finnzymes Oy, Espoo, Finland) was used for the PCR amplification. An In-fusion CF Dry-down PCR Cloning Kit (BD Biosciences, Palo Alto, CA, USA) was used to clone the fragment into the expression vector pCaHj505. The expression vector pCaHj505 contained the TAKA-amylase promoter derived from *Aspergillus oryzae* and the *Aspergillus niger* glucoamylase terminator elements. Furthermore pCaHj505 had pUC19 derived sequences for selection and propagation in *E. coli*, and an amdS gene, which encoded an acetoamidase gene derived from *Aspergillus nidulans* for selection of an amdS+*Aspergillus* transformant. Plasmid pCaHj505 was linearized by digestion with Bam I and Xho I, isolated by 1.0% agarose gel electrophoresis using TBE buffer, and purified using an illustra GFX PCR DNA and Gel Band Purification Kit (GE Healthcare, Buckinghamshire, UK) following the manufacturer's instructions.

For the gene amplification, the PCR reaction was performed which contained the primer pair, primer 1 & 2, and the genomic DNA of *Aspergillus niger* NN053297 as the template. In brief, 20 picomoles of each of the primer pair were used in a PCR reaction composed of 2 µl of genomic DNA, 10 µl of 5× Phusion® GC Buffer (Finnzymes Oy, Espoo, Finland), 1 µl of 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl with deionized water. The amplification was performed using a Peltier Thermal Cycler (MJ Research Inc., South San Francisco, CA, USA) programmed for denaturing at 98° C. for 1 minute; 10 cycles each of denaturing at 98° C. for 15 seconds, annealing at 68° C. for 30 seconds, with a 1° C. decrease per cycle and elongation at 72° C. for 3 minutes; 25 cycles each at 98° C. for 15 seconds, 58° C. for 30 seconds, and 72° C. for 3 minutes; and a final extension at 72° C. for 7 minutes. The heat block then went to a 4° C. soak cycle.

The PCR product, ~1.5 kb, was purified from solution by using an ILLUSTRA™ GFX™ PCR DNA and Gel Band Purification Kit.

The purified PCR product was then ligated to the linearized vector pCaHj505 by using In-Fusion™ Dry-down PCR Cloning Kit, resulting in p505-GH10_AnNz, in which the transcription of the of *Aspergillus niger* GH10 xylanase gene was under the control of a promoter from the gene for *Aspergillus oryzae* alpha-amylase. Briefly, for the ligation reaction, the pellet of In-Fusion Dry Down mix was suspended in 2 µl of double distilled H2O and 1 µl was taken to add to 0.3 µl of the linearized vector pCaHj505 and 3.7 µl PCR product in the tube. The ligation reaction was incubated at 50° C. for 15 min.

All 5 µl of the ligation solution were used for transformation of *E. coli* TOP10 competent cell (TIANGEN Biotech (Beijing) Co. Ltd., Beijing, China). The ligation solution was added to 50 µl of frozen-thaw competent cells and kept on ice for 30 minutes. Then the cells were heat-shocked at 42° C. for 1 min, and placed on ice for 2 min. Next, 200 µl of LB medium were added to the cells and incubated at 37° C. for 60 min shaking at 350 rpm in a thermomixer. Finally, all the cells were spread on LB plate containing 100 ug/ml of ampicillin and incubated at 37° C. overnight.

2 colonies were picked up for sequencing using 3730XL DNA Analyzers (Applied Biosystems Inc, Foster City, CA, USA). After the sequences were confirmed, the colony with correct insertion was inoculated for plasmid DNA extraction with a QIAPREP® Spin Miniprep Kit (QIAGEN GmbH, Hilden, Germany) by following the manufacturer's instruction. Thus the plasmid DNA of p505-GH10_AnNz was prepared for *A. oryzae* transformations in Example 5.

Example 5: Expression of the *Aspergillus niger* GH10 Xylanase Gene in *Aspergillus oryzae* MT3568

*Aspergillus oryzae* MT3568 protoplasts were prepared according to the method of Christensen et al., 1988, Bio/Technology 6: 1419-1422. For the transformations, 3 μg of plasmid DNA of p505-GH10_AnNz were used to transform *Aspergillus oryzae* MT3568. The transformation yielded several transformants. Four transformants were isolated and inoculated into 3 ml of Dap4C medium in 24-well plate and incubated at 30° C., 150 rpm. After 3 days incubation, 20 μl of supernatant from each culture were analyzed on NuPAGE Novex 4-12% Bis-Tris Gel w/MES (Invitrogen Corporation, Carlsbad, CA, USA) according to the manufacturer's instructions. The resulting gel was stained with Instant Blue (Expedeon Ltd., Babraham Cambridge, UK). SDS-PAGE profiles of the cultures showed that all 4 transformants had a protein band at 35 kDa. The transformant with the highest expression level of each gene was designated as 034EQ8.

Example 6: Preparation of an *Aspergillus niger* GH10 Xylanase 2 slants of the expression strain 034EQ8 used for inoculation of 12 flasks of 2-liter each containing 400 ml of Dap4C medium. In detail, each slant was washed with 10 ml of Dap4C medium and inoculated into 6 flasks, shaking at 30 C, 80 rpm. The culture was harvested on day 4 and filtered using a 0.22 μm DURAPORE Membrane (Millipore, Bedford, MA, USA). After purification the *Aspergillus niger* GH10 xylanase was obtained.

Example 7: Use of Enzyme in Wet Milling Process

The amount of starch and gluten separated from fiber, after incubation with and without enzyme, is measured by 10-g fiber assay. The 10-g fiber assay is generally described that it incubates wet fiber samples obtained from wet-milling plant after fiber pressing and re-suspended in lactic acid buffer to 200-g slurry containing 5% dry solids of fiber, which equals to the fiber content from 100 gram dry substance of corn, in the presence of enzymes, at conditions relevant to the process (pH 3.5 to 4, temperature around 52° C.) and over a time period of between 1 to 4 hr. After incubation the slurry is transferred and pressed over a sieve (typically 100 micron or smaller), while collecting the filtrate passing through. The fiber that retained over the sieve is pressed using a spatula to recover as much filtrate as possible. The pressed fiber is then transferred to a beaker containing 200-ml of water and stirred. The slurry is passed through the 75-micron sieve and the collected filtrate is combined with the first. The pressing, washing and filtering steps above is repeated once more, so that a final filtrate is recovered and combined with the first two. The combined filtrate is then vacuum filtered, this time through a glass micro filter paper (Whatman) which retains the insoluble solids that are released from the fiber and passed through the 75-micron screen. After passing 200 ml water over the filter paper to remove any trace of solubles, the total insoluble solids retained on the filter paper is dried and weighed. The dry weight is reported as Starch+Gluten released as percentage (w/w) of fiber dry matter of starting substrate.

Example 8: Use of GH10 Xylanase and/or GH62 Arabinofuranosidase 10-g fiber assay is performed at pH 3.8, incubating at 52° C. for 1 hour at dose of 35 ug enzyme protein per gram corn, using a blend including Celluclast and GH10 Xylanase A, in combination with either GH62 Arabinofuranosidase A or GH62 Arabinofuranosidase B. Blend consists of 5% GH62 Arabinofuranosidase A or GH62 Arabinofuranosidase B, 15% of GH10 Xylanase A, and the remaining 80% from Celluclast. For comparison, blend containing Celluclast and GH10 Xylanase A only (no GH62 Arabinofuranosidase) was included. The corn fiber with 13.63% residual starch and 10.44% residual protein was used as substrate in the fiber assay. Release of starch+gluten (dry substance) from corn fiber at the specified doses below was measured.

TABLE 1

| Treatments | Dose (ug enzyme protein/g corn) | Starch + Gluten Recovered |
|---|---|---|
| No Enzyme | 0 | 6.55% |
| Celluclast + GH10 Xylanase A | 35 | 8.90% |
| Celluclast + GH10 Xylanase A + GH62 Arabinofuranosidase A | 35 | 10.57% |
| Celluclast + GH10 Xylanase A + GH62 Arabinofuranosidase B | 35 | 10.73% |

As shown in table 1 the addition of GH62 Arabinofuranosidase A and GH62 Arabinofuranosidase B on top of Celluclast+GH10 Xylanase A can significantly increase the yield of starch+gluten in corn wet-milling process.

Example 9: Use of GH10 Xylanase and/or GH62 Arabinofuranosidase 10-g fiber assay is performed at pH 3.8, incubating at 52° C. for 1 hour at dose of 30 ug enzyme protein per gram corn, using a blend including Celluclast and GH10 Xylanase A, in combination with either GH62 Arabinofuranosidase A or GH62 Arabinofuranosidase B. Blend consists of 5% GH62 Arabinofuranosidase A or GH62 Arabinofuranosidase B, 15% of GH10 Xylanase A, and the remaining 80% from Celluclast. For comparison, blend containing Celluclast and GH10 Xylanase A only (no GH62) was included. The corn fiber with 16.67% residual starch and 10.77% residual protein was used as substrate in the fiber assay. Release of starch+gluten (dry substance) as well as individual starch and protein from corn fiber at the specified doses below was measured.

TABLE 2

| Treatments | Dose (ug enzyme protein/g corn) | Starch + Gluten Recovered | Individual Starch Recovered | Individual Protein Recovered |
|---|---|---|---|---|
| No Enzyme | 0 | 9.75% | 4.95% | 4.80% |
| Celluclast + GH10 Xylanase A | 30 | 13.95% | 8.29% | 5.66% |
| Celluclast + GH10 Xylanase A | 28.5 | 13.50% | 8.03% | 5.47% |
| Celluclast + GH10 Xylanase A + GH62 Arabinofuranosidase A | 30 | 15.40% | 9.58% | 5.82% |

TABLE 2-continued

| Treatments | Dose (ug enzyme protein/g corn) | Starch + Gluten Recovered | Individual Starch Recovered | Individual Protein Recovered |
|---|---|---|---|---|
| Celluclast + GH10 Xylanase A + GH62 Arabinofuranosidase B | 30 | 15.20% | 9.46% | 5.74% |

As shown in table 2 the addition of GH62 Arabinofuranosidase A and GH62 Arabinofuranosidase B on top of Celluclast+GH10 Xylanase A can significantly increase the yield of starch+gluten in corn wet-milling process.

Example 10: Use of GH10 Xylanase, GH30 Xylanase and/or GH62 Arabinofuranosidase

A 10-g fiber assay was performed at pH 3.8, with incubation at 52° C. for 1 hour and a dosage of 35 ug enzyme protein per gram corn, using enzyme blends containing GH10 Xylanase A, GH30 Xylanase A, GH62 Arabinofuranosidase A, and Celluclast with the detailed ratio of 35 ug EP/g corn as below table.

TABLE 3

| Treatments | Celluclast (ug-EP/g corn) | GH10 Xylanase A (ug-EP/g corn) | GH30 Xylanase A (ug-EP/g corn) | GH62 Arabinofuranosidase A (ug-EP/g corn) |
|---|---|---|---|---|
| No Enzyme | 0 | 0 | 0 | 0 |
| Celluclast | 35 | 0 | 0 | 0 |
| Celluclast + GH10 Xylanase A + GH62 Arabinofuranosidase A | 28 | 5.25 | 0 | 1.75 |
| Celluclast + GH10 Xylanase A + GH30 Xylanase A | 28 | 5.25 | 1.75 | 0 |
| Celluclast + GH30 Xylanase A + GH62 Arabinofuranosidase A | 28 | 0 | 5.25 | 1.75 |
| Celluclast + GH10 Xylanase A + GH30 Xylanase A + GH62 Arabinofuranosidase A | 28 | 3.5 | 1.75 | 1.75 |

For comparison, an enzyme composition containing only Celluclast was included. A corn fiber with 15.52% residual starch and 12.00% residual protein in fiber was used as substrate in the fiber assay. Release of starch+gluten (dry substance) from the corn fiber at the specified dosage was measured; the results are provided in the table 4 below.

TABLE 4

| Treatments | Dose (ug enzyme protein/g corn) | Starch + Gluten Recovered |
|---|---|---|
| No Enzyme | 0 | 4.39% |
| Celluclast | 35 | 6.68% |
| Celluclast + GH10 Xylanase A + GH62 Arabinofuranosidase A | 35 | 9.40% |
| Celluclast + GH10 Xylanase A + GH30 Xylanase A | 35 | 9.45% |
| Celluclast + GH30 Xylanase A + GH62 Arabinofuranosidase A | 35 | 8.55% |
| Celluclast + GH10 Xylanase A + GH30 Xylanase A + GH62 Arabinofuranosidase A | 35 | 9.70% |

As shown in table 4, the addition of combined GH62 Arabinofuranosidase A+GH30 Xylanase A on top of Celluclast+GH10 Xylanase A can significantly increase the yield of starch+gluten in corn wet-milling process.

Example 11: Preparation of Sterilized Palm Fruit Mesocarp

| Step | Action |
|---|---|
| 1 | In palm oil mill, oil palm FFBs (fresh fruit bunches) are received directly from the field, subjected to sterilization in industrial autoclave (120° C. for 120 minutes) and then threshed to obtain oil palm fruitlets along with calyx leaves. Collect the sterilized palm fruitlets. |
| 2 | Separate the oil palm fruitlets and discard the rest of the biomass [calyx leaves and small pieces of fruit bunch stalk (called as empty fruit bunch or EFB)]. |
| 3 | Pack the fruitlets in an autoclavable plastic cover and cook it in a kitchen pressure cooker (10 L Capacity; Aluminum) for below induction cooktop program: Program Name: Pressure Cooker Time: 30 minutes Watt/Temperature: 1300 W/180° C. |
| 4 | Spread the cooked fruitlets in a tray and allow it to cool down to approximately 50° C. |
| 5 | Peel off the mesocarp from the nut. Collect the mesocarp in a pre-weighed plastic storage container and record the weight. |
| 6 | Record the weight of nuts and discard it. |
| 7 | The peeled mesocarp is stored at 4° C. until use. |

Example 12: Preparation of Substrate

The sterilized palm fruit mesocarp is pressed:

| Step | Action |
|---|---|
| 1 | Mash required amount of mesocarp in mash bath at ~200 r.p.m. for: a. 3 minutes, if mesocarp quantity is more than 2 Kilograms. b. 2 minutes, if mesocarp quantity is 2-1 Kilograms. |
| 2 | Manually mix the mashed mesocarp until it is uniformly mixed |

Example 13: 10 Gins Assay Protocol for Palm Substrate 1. 10 g of prepared mash is aliquoted into 50 ml Falcon tubes with intermittent mixing to ensure substrate homogeneity. Note down the exact weight of substrate weighed;
2. Also, note down the empty weight of plastic pertriplates that are to be used for collecting extracted oil;
3. Pre-condition the tubes with substrate, keeping them at 90° C. for 5 minutes;
4. Transfer the tubes to respective incubation temperature (55° C.) water bath and pre-condition them for 10 minutes;
5. Inoculate the tubes with 500 μL of water in case of Control and 500 μL of enzyme solution in case of other enzyme treatments;
6. After adding enzyme/water, mix the contents with a microspatula 5 times in clock-wise and 5 times in anti-clockwise direction to ensure proper mixing;
7. Incubate for specified time (15 mins/30 mins) with intermittent mixing at every 15th minute of incubation with spatula, as specified in Step 6;

8. At the end of incubation, add 20 ml of water into each tube and mix well;
9. For clarification, transfer the tubes to 90° C. water bath and allow it to clarify for 30 mins;
10. Centrifuge the tubes in table top centrifuge at 7000 rpm, 30° C. for 10 min to get oil layer at the top;
11. Pipette out the oil layer into pre-weighed petriplates. Use hot water to completely extract free oil from each tube;
12. Note down the weight of petriplates with extracted oil;
13. The oil yield can by calculated by: Oil yield=Weight of petri dish containing oil extracted−Weight of empty petri dish.

TABLE 5

| Samples | mg Enzyme for 10 g substrate | Oil yield in grams |
|---|---|---|
| Control | no enzyme | 2.88 ± 0.2 |
| GH10 Xylanase A + GH62 Arabinofuranosidase A | 0.12 + 0.04 | 3.18 ± 0.1 |

As shown in table 5 the addition of GH10 Xylanase A and GH62 Arabinofuranosidase A can increase the oil yield from 10 gms of palm mesocarp.

What is claimed is:

1. A liquid formulation comprising:
   i) an enzyme blend comprising a beta-glucosidase, a cellobiohydrolase, an endoglucanase, a GH62 arabinofuranosidase, and a GH10 xylanase, wherein the arabinofuranosidase is present in an amount of 0.1-50 mg arabinofuranosidase protein per kg substrate (ppm), and wherein the xylanase is present in an amount of 0.1-50 mg xylanase protein per kg substrate (ppm); and
   ii) a formulating agent selected from the group consisting of a polyol, a salt, a sugar, and combinations thereof.

2. The liquid formulation of claim 1, wherein the arabinofuranosidase is present in an amount of 0.2-20 mg arabinofuranosidase protein per kg substrate (ppm), and wherein the xylanase is present in an amount of 0.2-20 mg xylanase protein per kg substrate (ppm).

3. The liquid formulation of claim 1, wherein the arabinofuranosidase is present in an amount of 0.1-1 mg arabinofuranosidase protein per kg substrate (ppm), and wherein the xylanase is present in an amount of 0.1-1 mg xylanase protein per kg substrate (ppm).

4. The liquid formulation of claim 1, wherein the arabinofuranosidase is present in an amount of 0.2-2 mg arabinofuranosidase protein per kg substrate (ppm), and wherein the xylanase is present in an amount of 0.2-2 mg xylanase protein per kg substrate (ppm).

5. The liquid formulation of claim 1, wherein the arabinofuranosidase is present in an amount of 0.5-5 mg arabinofuranosidase protein per kg substrate (ppm), and wherein the xylanase is present in an amount of 0.5-5 mg xylanase protein per kg substrate (ppm).

6. The liquid formulation of claim 1, wherein the arabinofuranosidase is present in an amount of 1-10 mg arabinofuranosidase protein per kg substrate (ppm), and wherein the xylanase is present in an amount of 1-10 mg xylanase protein per kg substrate (ppm).

* * * * *